United States Patent [19]

Demole

[11] 3,946,080

[45] Mar. 23, 1976

[54] FLAVOURING AND PERFUMING INGREDIENTS

[75] Inventor: Edouard P. Demole, Coppet, Switzerland

[73] Assignee: Firmenich SA, Geneva, Switzerland

[22] Filed: Apr. 2, 1975

[21] Appl. No.: 564,559

Related U.S. Application Data

[62] Division of Ser. No. 451,423, March 15, 1974.

[30] Foreign Application Priority Data

Apr. 10, 1973 Switzerland.......................... 5122/73
Apr. 12, 1973 Switzerland.......................... 5274/73

[52] U.S. Cl........ 260/593 R; 260/340.3; 260/340.5; 260/326.8; 260/594; 260/348 R; 131/2; 426/53 A; 426/536; 252/522; 260/635 R; 260/632 R

[51] Int. Cl.$^2$.......................................... C07C 49/12
[58] Field of Search................................. 260/593 R

[56] References Cited
OTHER PUBLICATIONS

Demole, et al., Helvetica Chimica Acta, Vol. 55, pp. 1866–1882 (1972).

Primary Examiner—Bernard Helfin
Assistant Examiner—James H. Reamer
Attorney, Agent, or Firm—Pennie & Edmonds

[57] ABSTRACT

Various compounds are disclosed to be useful in the flavouring of foodstuffs, animal feeds, beverages, pharmaceutical preparations and tobacco products. These compounds are equally useful perfuming ingredients.

1 Claim, No Drawings

FLAVOURING AND PERFUMING INGREDIENTS

This is a division of application Ser. No. 451,423 filed Mar. 15, 1974.

DESCRIPTION OF THE INVENTION

The compounds of the invention belong to the class of the derivatives listed below:
a. 6-methyl-3-isopropyl-hepta-4,6-dien-1-ol,
b. 8-hydroxy-5-isopropyl-non-6-en-2-one,
c. 5-isopropyl-non-3-ene-2,8-diol,
d. 8-hydroxy-5-isopropyl-nonan-2-one,
e. 5-isopropyl-nonane-2,8-diol,
f. 5-isopropyl-nonane-2,8-dione,
g. 3,4-epoxy-5-isopropyl-nonane-2,8-dione,
h. 8-hydroxy-5-isopropyl-8-methyl-non-6-en-2-one,
i. 6,7-epoxy-8-hydroxy-5-isopropyl-8-methyl-nonan-2-one,
j. 2-isopropyl-5-methyl-6,8-dioxa-bicyclo[3.2.1.]octan-7-yl-methyl-ketone,
k. 2-(2-isopropyl-5-methyl-6,8-dioxa-bicyclo[3.2.1-.]octan-7-yl)-propan-2-ol,
l. 6-isopropyl-1,3,3-trimethyl-2,9-dioxa-bicyclo[3.3.1.]nonan-4-ol, and
m. 1-(2-isopropyl-5-methyl-6,8-dioxa-bicyclo[3.2.1-.]octan-7-yl)-ethan-1-ol.

These compounds, which are new, may be regarded as derivatives of 5-isopropyl-8-methyl-nona-6,8-dien-2-one, better known under the name of solanone.

With the exception of 5-isopropyl-nonane-2,8-dione I have discovered the compounds of the invention as compounds of natural origin which can be isolated from an essential oil. This essential oil can be obtained by subjecting Burley tobacco to steam distillation, acidifying the aqueous distillate to about pH 4, and extracting the acidified distillate with a volatile solvent.

However, the procedure for isolating the compounds from tobacco is extremely complex and completely uneconomical. The yield of essential oil obtained is not higher than 0.03% by weight of the total tobacco treated. Moreover, the compounds of the invention are very minor constituents of the essential oil, having been detected therein at a concentration varying from about 0.005 to about 0.3% by weight. In order to isolate the desired compounds, the essential oil is subjected to a preliminary separation by fractional distillation under reduced pressure, and the less volatile fractions (b.p. above 35°C/0.001 Torr) are subjected to repeated fractional distillation using high resolution columns. For the final isolation of the desired compounds, it has been found necessary to resort to repeated separations by preparative gas chromatography, using stationary phases of contrasting polarity.

The disadvantages and difficulties inherent in the isolation of the cited compounds from an essential oil obtained from tobacco have been overcome by the realization of appropriate synthetic methods for their preparation. In this respect the specific procedures followed are described in the examples given hereinafter.

Broadly, the compounds of the invention can be used for improving, enhancing or modifying the flavouring properties of foodstuffs, animal feeds, beverages, pharmaceutical preparations and tobacco products, for improving, enhancing or modifying the odoriferous properties of perfumes and perfumed products, and for the preparation of fragrant and flavouring compositions.

Thus, the invention provides a flavouring or perfuming composition comprising one of the compounds listed above.

The invention also provides a tobacco or tobacco substitute having added thereto a small but flavouring effective amount of at least one of the compounds listed above.

In their pure state, the compounds of the invention possess original and characteristic flavouring and perfuming notes. They can develop or enhance a variety of flavour or aroma notes, particularly the woody note reminiscent of the typical character presented by dry leaves, with animal and sometimes fruity undertones.

These organoleptic characteristics make them particularly suitable for the aromatization of infusions or decoctions, such as those made from tea, camomile, lime or verbena.

A particular valuable feature of the pure compounds of the invention is that their tenacious organoleptic characters are stable and perfectly reproducible; whereas, in contradistinction, the properties of the natural essential oil vary with the origin of the tobacco from which it has been extracted, the method of extraction, and the purity of the essential oil recovered. Consequently, by virtue of their organoleptic properties, the compounds of the invention are useful as flavouring and perfuming ingredients over a wider field of applications than the natural essential oil.

The compounds of the invention are particularly useful for the flavouring of tobacco. The tobacco used, for example, in the manufacture of cigarettes comprises a mixture of different types, blended to give the desired characteristic flavour and aroma in the smoke produced. Thus, cigarettes currently manufactured usually contain mixtures of Virginia, Maryland and Kentucky tobacco in combination with oriental or turkish tobacco. The proportion of each type of tobacco in the mixture can be varied, in order to obtain the particular flavour and aroma desired. it is also common practice to employ flavouring agents and humectants as additives in these tobacco mixtures, further to enhance their organoleptic properties.

it has now been discovered that the addition of one of the compounds of the invention to a tobacco base (which may be natural tobacco, or a tobacco substitute of natural or synthetic origin) imparts thereto a dry leaf flavour, with woody, animal and sometimes fruity character. These properties are particularly developed on smoking the tobacco. it has however to be pointed out that the characterization of the flavour and aroma of tobacco smoke is rather subjective and different smokers may define in a different way the organoleptic characteristics of the very same tobacco.

The compounds of the invention can be used on their own, or in compositions comprising one or more flavouring or odoriferous compounds. The compounds and compositions of the invention may be used in a variety of form, depending upon their chemical nature, solubility and stability, but they are preferably used in solution. For the flavouring of tobacco, they are preferably added after ageing, curing and shredding, but before the tobacco is formed into cigarettes or other finished products. A convenient method for flavouring tobacco consists in spraying it with a solution of the flavouring compound or composition in alcohol, or in a mixture of alcohol and propylene glycol.

For the perfumery, the compounds of the invention are particularly suitable for developing herbacious type notes, specifically those reminiscent of hay. More particularly, it has been found that by the use of 2-(2-isopropyl-5-methyl-6,8-dioxa-bicyclo[3.2.1]octan-7-yl)-propan-2-ol, 8-hydroxy-5-isopropyl-non-6-en-2-one or 8-hydroxy-5-isopropyl-8-methyl-non-6-en-2-one as perfuming agents it was possible to develop herbacious type notes of particular interest.

The proportions in which the flavouring agents of the invention are used in flavouring compositions or are added to tobacco can vary widely, depending upon the specific organoleptic effect it is desired to achieve and the type of tobacco to which they are added. Interesting flavouring effects can be achieved with amounts ranging from 1 to 500 ppm, preferably from 10 to 200 ppm and most preferably from 10 to 50 ppm, based on the weight of the product flavoured.

Comparable proportions of the compounds of the invention can be used for the flavouring of foodstuffs, beverages, animal feeds and pharmaceutical preparations.

When the compounds of the invention are used for the preparation of artificial flavour compositions, they may tipycally constitute up to 80% by weight of the composition.

Similarly, when used as perfuming ingredient, the proportion of the compounds of the invention in the perfume composition or perfumed product to which they are incorporated can vary over a wide range. Interesting odoriferous effects can be achieved with amounts ranging from 1 to 10% of the total weight of the composition.

In all cases, the ranges mentioned can be varied, in order to achieve specific odoriferous or flavouring effects.

The invention is better illustrated by the following examples, wherein the temperatures are indicated in degrees centigrade and the abbreviations have the meaning common in the art. It has to be appreciated however that the invention is not deemed to be limited by the given examples.

1. 6-Methyl-3-isopropyl-hepta-4,6-dien-1-ol a. 17.2 g (0.2 M) of isovalerianic aldehyde were added under stirring during 75 min. to a mixture of 28.4 g (0.4 M) of pyrrolidine and 8 g of anhydrous potassium carbonate. The temperature of the reaction mixture was kept during the addition at 4°–6°, whereupon it was increased to 20° while stirring and kept at this value during 75 min. The reaction mixture was filtered and the precipitate was washed with ether while the organic clear filtrate by evaporation gave a residue which upon distillation under reduced pressure yielded 23 g (83%) of the enamine of formula $$(CH_3)_2—CH—CH=CH—N\overset{\frown}{\underset{\smile}{\phantom{x}}}$$

B.p. 62°–4°/10 Torr.

b. 5.0 g (71.5 mM) of methylvinylketone in 10 ml of anhydrous ether were added during 45 min. to a solution kept under nitrogen of 9.0 g (65 mM) of the enamine prepared above in 50 ml of anhydrous ether. The reaction mixture was kept during 24 h at room temperature under nitrogen atmosphere, whereupon 1.95 ml of water and about 11.2 ml of a 6N aqueous solution of hydrochloric acid were added thereto in such a way as to adjust the pH value to about 5–6. After 1 h of supplemental stirring at room temperature the reaction mixture was extracted twice with ether, washed with a 1% aqueous solution of hydrochloric acid followed by a washing with a 5% aqueous solution of sodium bicarbonate, and finally with a NaCl saturated solution in water until neutrality. The extract finally obtained was rapidly distilled at mild temperature to give 6.6 g (65%) of 5-oxo-2-isopropyl-2-hexanal;

B.p. 47°–9°/0.001 Torr.
IR: 2730, 2900, 1715, 1360 cm$^{-1}$
MS: M–18 = 138
NMR: 0.96 (6H); 2.07 (3H); 1.5–2.6 (6H); 9.55 (1H) δ ppm c. 23.4 g (0.15 M) of the keto-aldehyde obtained as indicated above, 15.4 g (0.24 M) of ethylene-glycol and 0.15 g of p-toluenesulfonic acid in 150 ml of benzene were brought to the boiling for 30 min. The reaction mixture after the usual treatments of washing, drying and evaporation of the volatile components, was distilled under reduced pressure at 0.001 Torr. 21.2 g (70%) of the ketal of formula were obtained. The purity of this compound was found to be of the order of 60–70% as revealed by vpc.

B.p. 60°–1°/0.001 Torr.
IR (film): 1120, 1360, 1710 cm$^{-1}$,
MS: M$^+$ = 200;
NMR: 0.85 (3H, $d$, $J$=2.5 cps); 0.98 (3H, $d$, $J$=2.5 cps); 1.2–1.8 (4H, $m$); 2.03 (3H, $s$); 2.46 (2H, $t$, $J$=6.5 cps); 3.80 (4H, $m$); 4.65 (1H, $d$, $J$=4.5 cps) δ ppm.

d. A solution of 21.2 g (0.084 M) of the ketal obtained in accordance with the procedure described under letter (c) and 52 g (0.256 M) of m-chloroperbenzoic acid at 85% in 1 lt. of chloroform was left in the dark at room temperature during 12 days. The reaction mixture was then concentrated in vacuum, whereupon ether was added thereto. After filtration and washing of the clear filtrate with a 5% solution of sodium carbonate, 18 g of the raw product were obtained. This compound was then dissolved in 100 ml of dioxan and 40 ml of 5% aqueous sulphuric acid. A solution was thus obtained which was then left 24 h at room temperature, whereupon sodium chloride was added and the product extracted twice with ether. The combined organic extracts were washed with water until neutrality, dried over sodium sulphate and evaporated to dryness to yield a residue which on fractional distillation gave 6.5 g (23.8%) of a product having B.p. 50°–65°/0.001 Torr. This product contained 53.6% of the ester-aldehyde of formula e. 5.5 g of a 14% solution of n-butyl-lithium in hexane were added in a nitrogen atmosphere under stirring during 45 min. to a mixture containing 4.65 g (13 mM) of methallyl-triphenylphosphonium chloride in 40 ml of ether. The temperature of the reaction mixture was kept between 6° and 10° during the whole addition and it was then increased to room temperature and kept at this value for 4 h. After cooling to −70° 1.72 g (5.3 mM) of the esteraldehyde prepared according to paragraph (d) hereinabove in 5 ml of ether were added to the reaction mixture by taking care that the temperature does not increase above −50°. After having been left at said temperature for 3 h and at 20° during one night, the mixture was diluted with water and then extracted with ether, whereupon the combined organic extracts were subjected to the usual treatments of washing and drying. The residue obtained on evaporation of the volatile components was then treated at reflux during 1 h with 50 ml of a 1N solution of potassium hydroxide in ethanol. By extraction with ether followed by the usual treatments on the ether extracts, 1.5 g of a product were obtained. This product by purification by means of column chromatography (30 g of silica gel; eluant: benzene) gave 0.58 g (65%) of 6-methyl-3-isopropyl-hepta-4,6-dien-1-ol the purity of which was of ca. 95%. B.p. ca. 60°/0.001 Torr.

$d_4^{20} = 0.8833$; $n_D^{20} = 1.4805$

IR: 3340, 3090, 1760, 1630, 1600, 1040, 960 and 870 cm$^{-1}$,

UV: $\lambda_{max}^{EtOH} = 230$ nm ($\epsilon = 24,195$)

SM: M$^+$= 168

NMR: 0.80 (3H); 0.91 (3H); 1.80 (3H, s); 1.2–2.4 (4H); 3.47 (2H); 3.80 (1H); 4.81 (2H); 5.33 (1H); 6.05 (1H) δ ppm.

2. 8-Hydroxy-5-isopropyl-non-6-en-2-one 6.51 g (17.8 mM) of the ketal of formula

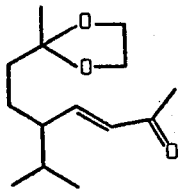

were added under vigorous stirring to a suspension kept at 20°–25° of 0.455 g (12 mM) of lithiumaluminiumhydride in 30 ml ether. After 4 h of supplemental stirring the excess of lithiumaluminiumhydride was decomposed with moist ether, whereupon the reaction mixture was poured onto a concentrated solution of ammonium chloride. After the usual treatments 6.5 g of a product were obtained. This product was then treated at 20° under nitrogen atmosphere with 50 ml of a 5% aqueous solution of sulphuric acid in 50 ml of ether. The separated organic phase was evaporated to give 5 g of a residue which on purification by column chromatography (100 g of silica gel; eluant: a mixture of benzene and ethyl acetate, the concentration of which varies in between 95:5 and 3:2) yielded 3.4 g (96%) of 8-hydroxy-5-isopropyl-non-6-en-2-one; B.p. 80°/0.001 Torr;

$d_4^{20} = 0.9261$; $n_D^{20} = 1.4608$

IR: 3450, 1710, 1360, 1050 and 975 cm$^{-1}$;

MS: M-18 = 180;

NMR (CDCL$_3$): 0.87 (6H); 1.26 (3H); 1.0–2.0 (5H); 2.13 (3H); 2.40 (2H); 4.30 (1H); 5.45 (2H) δ ppm.

The ketal used as starting material for the preparation given above can be synthetized as follows:

a. 10.1 g (64.7 mM) of 5-oxo-2-isopropyl-2-hexanal (prepared according to paragraph (b) of the above given example) were refluxed during 4 days under nitrogen atmosphere with 22.2 g (69.7 mM) of the ylid obtained by the reaction between triphenylphosphine and chloracetone in 75 ml of anhydrous benzene (see: J. Org. Chem. 22, 41 (1957)).

The reaction mixture was then concentrated to dryness and the obtained residue taken up with about 200 ml of petrol ether (B.p. 30°–50°) and the precipitate separated by filtration. On evaporation of the clear filtrate followed by fractional distillation of the obtained residue, 10.9 g of 5-isopropyl-non-3-en-2,8-diene were obtained; B.p. 70°–84°/0.001 Torr. b. A mixture of 5-isopropyl-non-3-en-2,8-dione (7.0 g; 35.7 mM), 0.040 g of p-toluenesulfonic acid, 2.46 g of ethylene-glycol in 40 ml of benzene was refluxed in a Dean & Stark type separator during 1½ h. The reaction mixture was then washed with a 5% aqueous solution of sodium bicarbonate, then with water before being subjected to the usual treatments of extraction with ether, washing and drying of the organic extracts. On evaporation of the organic phase, 7.72 g of the desired monoketal were obtained. This product showed a purity of about 60–70%; B.p. 87°–90°/0.001 Torr.

IR: 1675, 1620, 1360 and 980 cm$^{-1}$;

NMR (CCl$_4$): 0.88 (6H); 1.19 (3H); 2.15 (3H); 1.0–2.2 (6H); 3.80 (4H); 5.87 (1H); 6.46 (1H) δ ppm 3. 5-Isopropyl-non-3-ene-2,8-diol 2.5 g of 5-isopropyl-non-3-ene-2,8-dione, prepared in accordance with the method described in paragraph (a) of the previous example, in 10 ml of anhydrous ether were added to a mixture of 0.292 g (7.7 mM) of lithiumaluminiumhydride in 10 ml of ether and 10 ml of tetrahydrofuran. The reaction mixture was left under stirring at 20° overnight, then it was poured onto a concentrated aqueous solution of ammonium chloride, extracted and treated as usual. The obtained residue was purified by column chromatography (50 g of silica gel; eluant: ether/petrol ether) to yield the desired diol (1.3 g: yield 51%); B.p. 102°/0.001 Torr; $n_D^{20} = 1.4645$; $d_4^{20} = 0.9275$; IR: 3350, 1120, 1060 and 970 cm$^{-1}$;

NMR (CCL$_4$): 0.67 (1H, s); 0.75–1.00 (6H, m); 1.16 (6H, t apparent, J=7.5 cps); 1.0–2.5 (6H, m); 2.8–4.5 (3H, very broad s); 5.37 (2H, m) δ ppm.

4. 8-Hydroxy-5-isopropyl-nonan-2-one

A mixture of 1.74 g (8.7 mM) of 5-isopropyl-nonane-2,8-dione, which can be prepared according to the method described in example 6 hereinafter, 0.545 g (8.7 mM) of ethylene-glycol, 0.020 of p-toluenesulfonic acid in 20 ml of benzene was refluxed during 1½ h in a Dean & Stark type separator. The usual treatments of extraction with ether, washing, drying and evaporation afforded 2.2 g of a mixture mainly containing a monoketal of formula

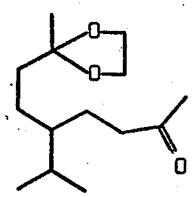

This mixture was then reduced by means of 0.175 g (4.6 mM) of lithiumaluminiumhydride in ether at 20° during 20 h. After the usual treatments of decomposition of the excess of lithiumaluminiumhydride the reaction mixture was treated with 6 ml of a 5% aqueous sulphuric acid in 20 ml of dioxan. By extraction with ether followed by washing, drying and evaporation of the combined extracts there was obtained a residue (2 g) which on purification by column chromatography (40 g of silica gel; eluant; a mixture of benzene and ethyl acetate 95:5) gave 0.60 g (34%) of 8-hydroxy-5-isopropyl-nonan-2-one; B.p. 90°/0.001 Torr;

$d_4^{20} = 0.9368$; $n_D^{20} = 1.4589$

IR: 3450, 1705, 1360 cm$^{-1}$

NMR (CDCl$_3$): 0.84 (6H, $d$, J=6 cps); 1.19 (3H, $d$, J=6 cps); 0.9–1.9 (9H, $m$); 2.15 (3H, $s$); 2.44 (2H, $t$, J=8 cps); 3.78 (1H, $m$) δ ppm.

5. 5-Isopropyl-nonane-2,8-diol 2.5 g (12.6 mM) of 5-isopropyl-nonane-2,8-dione, which can be prepared according to the process described in example 6 hereinafter, in 10 ml of anhydrous ether were added to a mixture of 0.570 g (50 mM) of lithiumaluminiumhydride in 10 ml of ether and 10 ml of tetrahydrofuran. The reaction mixture was kept under stirring overnight at 20° and poured then onto a saturated aqueous solution of ammonium chloride. After the usual treatments of extraction, washing and drying followed by evaporation of the volatile portions there was obtained a residue which on fractional distillation gave 2.3 g (90%) of the desired diol; B.p. 120°/0.001 Torr;

$d_4^{20} = 0.9388$; $n_D^{20} = 1.4631$

IR: 3370 and 1120 cm$^{-1}$;

NMR (CCl$_4$): 0.85 (6H, $d$, J=6 cps); 1.13 (6H, $d$, J=6 cps); 1.0–2.2 (10H, $m$); 3.3–4.5 (4H, $m$) δ ppm

6. 5-Isopropyl-nonane-2,8-dione 1.96 g (10 mM) of 5-isopropyl-non-3-ene-2,8-dione, prepared according to the method described in paragraph (a) of example 2, in 20 ml of ethyl acetate were reduced by catalytic hydrogenation in the presence of 0.196 g of palladium at 10% over charcoal. After filtration and evaporation of the volatile portions, a residue was obtained which by fractional distillation gave 1.77 g (89%), of the desired dione;

B.p. 80°/0.001 Torr;
$d_4^{20} = 0.9292$; $n_D^{20} = 1.4501$
IR: 1710 and 1360 cm$^{-1}$;
MS: M-18 = 180;

NMR (CCl$_4$): 0.85 (6H, $d$, J=6 cps); 1.0–1.9 (6H, $m$); 2.05 (6H, $s$); 2.37 (4H, $t$, J=7 cps) δ ppm.

7. 3,4-Epoxy-5-isopropyl-nonane-2,8-dione

A solution of 16.25 g (ca. 40 mM) of the keto-ketal prepared in accordance with the procedure described in example 2, in 125 ml of anhydrous ether was added during 50 min. at room temperature to a mixture of 1.14 g (30 mM) of lithiumaluminiumhydride in 75 ml of anhydrous ether. The reaction mixture was then stirred during 4 h and subsequently the excess of lithiumaluminiumhydride was decomposed with moist ether, whereupon the mixture was poured into a concentrated aqueous solution of ammonium chloride. By the usual treatments of extraction with ether, washing, drying and evaporation of the organic extracts, 16 g of a product were obtained, the analytical data of which were the following:

IR: 3450, 1050, 965 cm$^{-1}$;
MS: M-15 = 227;

NMR (CCl$_4$): 0.85 (6H, $m$); 1.17 (3H, $d$, J=6 cps); 1.18 (3H, $s$); 1.0–2.3 (6H, $m$); 3.78 (4H, $s$); 3.9–4.5 (2H, $m$); 5.2–5.5 (2H, $m$) δ ppm The product thus obtained was dissolved in 20.4 g (100 mM) of m-chloroperoxybenzoic acid at 85% in 380 ml of chloroform. After having been left 24 h at 20°, the reaction mixture was evaporated to dryness under reduced pressure and the residue was taken up with petrol ether (B.p. 30°–50°), and the organic phase washed with a 5% aqueous solution of sodium carbonate followed by a concentrated aqueous solution of sodium chloride.

After the usual treatments, there was obtained the 3,4-epoxy-5-isopropyl-2-hydroxy-nonan-8-one ketal (18 g). This product was treated with 160 g of MnO$_2$, previously activated during 20 h at 120°, in 1.4 l of benzene in nitrogen atmosphere. After 2 days of stirring at 20°, the mixture was filtered and the clear filtrate evaporated to dryness. There was thus obtained a residue which was then treated with 2% aqueous sulphuric acid in a mixture of ether and dioxan (1:1:1). This mixture was extracted with ether and the organic extracts were subjected to the usual treatments to give 11 g of 3,4-epoxy-5-isopropyl-nonane-2,8-dione which on purification by means of column chromatography (silica gel; eluant: petrol ether:ether 9:1 to 1:1) gave the desired diketo-epoxide in its pure state.

B.p. 90°/0.001 Torr. $d_4^{20} = 1.0105$; $n_D^{20} = 1.4594$
IR (CCl$_4$): 1700, 1355, 1240, 1160 and 860 cm$^{-1}$
MS: M-43 = 169;

NMR (CDCl$_3$): 0.95 (6H, 2$d$); 1.11–2.00 (4H, $m$); 2.09 (3H, $s$); 2.18 (3H, $s$); 2.65 (2H, $t$, J=7.5 cps); 2.85 (1H, $d$ of $d$, J=8.5 cps, J'=ca. 2 cps); 3.19 (1H, $d$, J=ca. 2 cps) δ ppm

8. 8-Hydroxy-5-isopropyl-8-methyl-non-6-ene-2-one 7.2 g (18 mM) of the monoketal prepared in accordance with the procedure described in example 2, in 20 ml of ether were added to a mixture of 1.09 (45 mM) of magnesium turnings, 60 ml of anhydrous ether and an excess of methyl bromide according to the usual technique applied for the Grignard type reactions. The reaction mixture was then refluxed for 1 h and left at room temperature overnight, whereupon it was poured into an icy 5% aqueous solution of sulphuric acid. After having been left at room temperature for 2½ h more, the organic phase was separated and subjected to the usual treatments of washing with a 5% aqueous solution of sodium carbonate followed by a further washing with water. After drying and evaporation, 7 g of a raw material were obtained which by purification by means of column chromatography gave 3.06 g (44%) of the desired product.

B.p. 85°/0.001 Torr; $d_4^{20} = 1.4600$
IR: 3450, 1700, 1360, 1150 and 970 cm$^{-1}$;
MS: M-18 = 194;

NMR (CCl$_4$): 0.85 (6H, 2d); 1.22 (6H, $s$); 2.03 (3H, $s$); 1.1–2.0 (4H, $m$); 2.1–2.5 (3H, $m$); 5.23–5.50 (2H, $m$) δ ppm.

9.
6,7-Epoxy-8-hydroxy-5-isopropyl-8-methyl-nonan-2-one.

2.96 g of 8-hydroxy-5-isopropyl-8-methyl-non-6-en-2-one (13.9 mM) were treated with 3.4 g (16.7 mM) of m-chloroperoxybenzoic acid at 85% in 90 ml of chloroform. The reaction mixture was kept during 72 h at 20° whereupon it was concentrated at low temperature and the obtained residue taken up with petrol ether. After filtration, the clear filtrate was subjected to the usual treatments to give 3 g of the desired raw epoxy-ketone. By purifying this compound by means of column chromatography, 2.51 g of a pure compound were obtained.

B.p. 100°/0.001 Torr; $d_4^{20} = 0.9905$; $n_D^{20} = 1.4572$
IR: 3400, 1360, 1705, 1165, 960 and 900 cm$^{-1}$;
MS: M-59 = 169;
NMR (CDCl$_3$): 0.96 (3H, d, J=6 cps); 1.23 (3H, s); 1.27 (3H, s); 2.13 (3H, s); 1.15–2.10 (5H, m); 2.3–3.0 (4H, m) δ ppm.

10.
2-Isopropyl-5-methyl-6,8-dioxa-bicyclo[3.2.1]Octan-7-yl-methyl-ketone 0.50 g (2.38 mM) of 3,4-epoxy-5-isopropyl-nonane-2,8-dione prepared according to the process described in example 7, in 10 ml of benzene were refluxed in the presence of 0.020 g of p-toluenesulfonic acid during 4 h. After a supplemental addition of 0.020 g of p-toluenesulfonic acid the reaction mixture was refluxed for 3 h more. By extraction with ether followed by the usual treatments of the separated organic extracts, 0.315 g (63%) of the desired ketal were obtained. B.p. 80°/0.001 Torr; $n_D^{20} = 1.4608$; $d_4^{20} = 1.0324$ IR (CCl$_4$): 1700 and 1375 cm$^{-1}$;
MS: M-43 = 169;
NMR (CDCl$_3$): 1.00 (6H, m); 1.58 (3H, s); 1.0–2.0 (6H, m); 2.25 (3H, s); 4.24 (1H, s); 4.55 (1H, m) δ ppm.

The product is under the form of a mixture of its two stereoisomers of formula

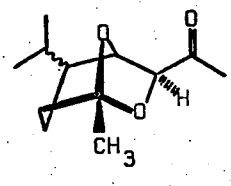

11.
2-(2-Isopropyl-5-methyl-6,8-dioxa-bicyclo[3.2.1]octan-7-yl)-propan-2-ol (A) and 6-isopropyl-1,3,3-trimethyl-2,9-dioxa-bicyclo[3.3.1-]nonan-4-ol (B)

2.1 g (9.2 mM) of the epoxy-ketol prepared according to the procedure described in example 9, in 45 ml of benzene were refluxed with 0.045 g of p-toluenesulfonic acid during 2 h according to the conditions used in the course of the preparation described in example 10 hereinabove. 2.2 g of a raw material were thus obtained which on purification by column chromatography (silica gel; eluant: petrol ether: ether 4:1) gave 1.2 g of a mixture of 2 hydroxy-ketals. These latter can be separated by vpc (CARBOWAX $^R$ 5%; 200°; 2.5 m).

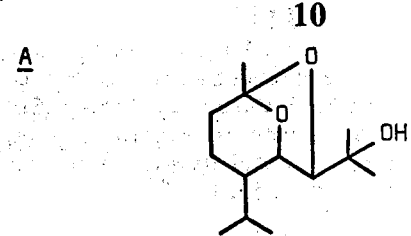

IR (CCl$_4$): 3500, 1030 cm$^{-1}$;
MS: M-59 = 169;
NMR (CDCl$_3$): 1.00 (6H, d, J=6 cps); 1.22 (3H, s); 1.38 (3H, s); 1.46 (3H, s); 2.13 (1H, s); 1.1–2.3 (6H, m); 3.78 (1H, d, J=4 cps); 4.28 (1H, d, J=ca. 4 cps) δ ppm

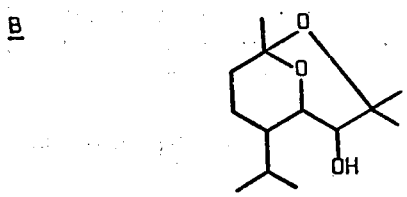

IR: 3500 and 1025 cm$^{-1}$;
MS: M-43 = 185;
NMR (CDCl$_3$): 0.98 (6H, t apparent, J=5.5 cps); 1.27 (3H, s); 1.33 (3H, s); 1.46 (3H, s); 1.1–1.8 (6H, m); 2.05 (1H, d, J=7 cps); 3.55 (1H, d of d, J=7 cps, J'=3 cps); 4.04 (1H, broad s) δ ppm.

2-(2-Isopropyl-5-methyl-6,8-dioxa-bicyclo[3.2.1]octan-7-yl)-propan-2-ol prepared hereinabove occurs under the form of a mixture of stereoisomers of formula

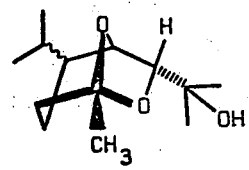

These latter correspond to the product as directly isolated from the essential oil of Burley tobacco.

By means of a separate synthesis it has been possible to prepare the mixture of the isomers defined by the following formula

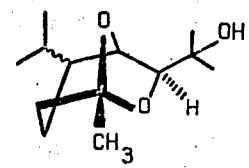

as follows:

A solution of methylmagnesium bromide was prepared according to the usual technique of the Grignard type reactions by treating 0.109 g (4.5 mM) of magnesium metal with 10 ml of an ether solution containing 0.475 g (5 mM) of methyl bromide. To this solution 0.850 g (4 mM) of the ketal prepared according to example 10, dissolved in 5 ml of anhydrous ether, were added, whereupon the mixture was refluxed during 1 h and decomposed then with a saturated aqueous solution of ammonium chloride. After the usual treatments of extraction with ether, washing, evaporation and purification of the obtained residue by column chromatography (17 g of silica gel; eluant: petrol ether:ether 9:1) there was obtained a mixture of two stereoisomers which could then be separated by preparative vpc (CARBOWAX [R] 5%; 200°; 2.5 m).

Isomer I:

IR: 3500, 1020 and 845 cm$^{-1}$;

NMR (CDCl$_3$): 1.00 (6H, $t$ apparent, J=6 cps); 1.19 (6H, $s$); 1.44 (3H, $s$); 1.3–2.1 (6H, $m$); 2.06 (1H, $s$); 3.78 (1H, $s$); 4.43 (1H, broad $s$) δ ppm

Isomer II:

IR: 3500, 1020 and 855 cm$^{-1}$;

NMR (CDCl$_3$): 0.93 (6H, $t$ complex band); 1.17 (6H, $s$); 1.46 (3H, $s$); 1.0–1.9 (6H, $m$); 2.10 (1H, $s$); 3.80 (1H, $s$); 4.38 (1H, broad $s$) δ ppm.

12. 1-(2-Isopropyl-5-methyl-6,8-dioxa-bicyclo[3.2.1]octan-7-yl)-ethan-1-ol 0.1 g (0.47 mM) of the keto-ketal, prepared according to example 10 hereinabove, in 3 ml of methanol was reduced by means of 0.01 g of sodium borohydride. The reaction mixture was then concentrated under reduced pressure and the obtained residue taken up with a 10% aqueous solution of hydrochloric acid, extracted with ether, washed with an aqueous solution of sodium bicarbonate (5%) and finally with water until neutrality. The usual treatments gave the desired product under the form of a mixture of stereoisomers which could be characterized as follows:

Isomer I:

NMR: 1.00 (6H, 2d); 1.15 (3H, $d$, J=6 cps); 1.44 (3H, $s$); 1.3–2.2 (6H, $m$); 2.51 (1H, broad $s$); 3.53–3.84 (2H, $m$); 4.29 (1H, broad $s$) δ ppm.

Isomer II:

NMR: 0.95 (6H, $m$); 1.20 (3H, $d$, J=6 cps); 1.44 (3H, $s$); 1.0–2.0 (7H, $m$); 3.55–3.95 (2H, $m$); 4.49 (1H, broad $s$) δ ppm

Isomer III:

NMR: 0.95 (6H, $m$); 1.15 (3H, $d$, J=6 cps); 1.46 (3H, $s$); 1.0–2.0 (6H, $m$); 2.60 (1H, broad $s$); 3.44–3.85 (2H, $m$); 4.25 (1H, broad $s$) δ ppm These isomers may be represented by the following formula

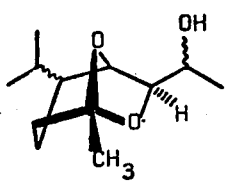

13. Aromatization of Tobacco 10 g of an American blend tobacco mixture were sprayed with 0.5 g of a 1% solution of 8-hydroxy-5-isopropyl-non-6-en-2-one in 95% ethanol, and the tobacco thus flavoured was used to manufacture "test" cigarettes. As a control, cigarettes were also manufactured from the same tobacco mixture, sprayed with 95% ethanol alone. The smoke from the cigarettes was subjected to organoleptic evaluation by a panel of flavour experts, who unanimously stated that the smoke of the flavoured cigarettes possessed a characteristic woody note, particularly interesting for the reconstitution of the "cigar" aroma. Other samples were equally evaluated in accordance with the same procedure and by using the same proportions. The following table gives a list of the products thus evaluated together with the mention of the developed flavour.

TABLE

| Compound | organoleptic evaluation [1] |
|---|---|
| a | woody |
| b | see example 13 |
| c | powerful, tobacco character, reminiscent of the note of cigar |
| d | woody, dry |
| e | woody, animal |
| f | woody, animal |
| g | slightly fruity |
| h | woody, dry, tobacco character |
| i | tobacco notes of Virginia type |
| j | hay note |
| k | woody, green |
| l | burnt, animal |
| m | woody |

[1] The organoleptic characters mentioned refer to the properties of the tested compounds on tobacco relative to the same tobacco unflavoured.

14. Perfume Composition Of The Type "Classic Eau de Cologne"

A base perfume composition of "Classic Eau de Cologne" type was prepared by admixing the following ingredients (parts by weight):

| | |
|---|---:|
| Lemon oil | 250 |
| Bergamot artificial oil | 250 |
| Sweet orange oil | 100 |
| Petitgrain bigarade | 100 |
| Lavender | 90 |
| Neroli bigarade | 10 |
| Muscone 10 %* | 100 |
| Total | 900 |

*in 95 % ethanol

By adding to 90 parts by weight of the above given base perfume composition 10 parts by weight of 8-hydroxy-5-isopropyl-non-6-en-2-one, a novel composition was obtained. This composition possessed an enhanced odour of witch hazel type with a pleasant character of hay.

By substituting in the above example 8-hydroxy-5-isopropyl-8-methyl-non-6-en-2-one or 2-(2-isopropyl-5-methyl-6,8-dioxa-bicyclo[3.2.1]octan-7-yl)-propan-2-ol for 8-hydroxy-5-isopropyl-non-6-en-2-one, similar effects were observed.

I claim:
1. 5-isopropyl-nonane-2,8-dione.

* * * * *

UNITED STATES PATENT AND TRADEMARK OFFICE
CERTIFICATE OF CORRECTION

PATENT NO. : 3,946,080
DATED : March 23, 1976
INVENTOR(S) : Edouard P. Demole

It is certified that error appears in the above-identified patent and that said Letters Patent are hereby corrected as shown below:

Column 1, line 24 "[3.3.1.]" should be --[3.3.1]--

Column 2, line 39 "it" should be --It--

Column 2, line 43 "it" should be --It--

Column 2, line 49 "it" should be --It--

Column 5, line 68 "NMR ($CDCL_3$)" should be --NMR ($CDCl_3$)=-

Column 6, line 48 "NMR ($CCL_4$)" should be --NMR ($CCl_4$)--

Column 12, line 4 "1%" should be --1 °/oo--

Signed and Sealed this

Seventh Day of September 1976

[SEAL]

*Attest:*

RUTH C. MASON
*Attesting Officer*

C. MARSHALL DANN
*Commissioner of Patents and Trademarks*